(12) United States Patent
Kojima et al.

(10) Patent No.: US 9,149,532 B2
(45) Date of Patent: Oct. 6, 2015

(54) PHARMACEUTICAL COMPOSITION (71) Applicant: DAIICHI SANKYO COMPANY, LIMITED, Chuo-ku (JP)

(72) Inventors: Masazumi Kojima, Shinagawa-ku (JP); Yoshio Kuno, Shinagawa-ku (JP); Hiroaki Nakagami, Shinagawa-ku (JP); Shinji Sagasaki, Shimada (JP); Koichi Ishidoh, Hiratsuka (JP); Gaku Sekiguchi, Hiratsuka (JP)

(73) Assignee: Daiichi Sanykyo Company, Limited, Tokyo (JP)

( * ) Notice: Subject to any disclaimer, the term of this patent is extended or adjusted under 35 U.S.C. 154(b) by 0 days.

(21) Appl. No.: 13/968,776

(22) Filed: Aug. 16, 2013

(65) Prior Publication Data

US 2013/0337064 A1     Dec. 19, 2013

Related U.S. Application Data

(63) Continuation of application No. 12/569,057, filed on Sep. 29, 2009, now abandoned, which is a continuation of application No. PCT/JP2008/000791, filed on Mar. 28, 2008.

(30) Foreign Application Priority Data

Mar. 29, 2007   (JP) ................................. 2007-087327

(51) Int. Cl.
| | | |
|---|---|---|
| A01N 43/00 | (2006.01) |
| A61K 31/33 | (2006.01) |
| A61K 47/26 | (2006.01) |
| A61K 9/20 | (2006.01) |
| A61K 31/444 | (2006.01) |
| A61K 9/28 | (2006.01) |

(52) U.S. Cl.
CPC ............... *A61K 47/26* (2013.01); *A61K 9/2018* (2013.01); *A61K 9/2027* (2013.01); *A61K 9/2054* (2013.01); *A61K 9/2059* (2013.01); *A61K 9/2866* (2013.01); *A61K 31/444* (2013.01)

(58) Field of Classification Search
None
See application file for complete search history.

(56) References Cited

U.S. PATENT DOCUMENTS

| | | | |
|---|---|---|---|
| 4,361,545 A | 11/1982 | Powell et al. |
| 5,202,129 A | 4/1993 | Semejima et al. |
| 5,506,248 A | 4/1996 | Nikfar et al. |
| 5,958,453 A | 9/1999 | Ohno et al. |
| 7,081,256 B2 | 7/2006 | Kubota et al. |
| 7,342,014 B2 | 3/2008 | Ohta et al. |
| 7,576,135 B2 | 8/2009 | Ohta et al. |
| 7,605,180 B2 | 10/2009 | Ninomiya et al. |
| 2002/0160048 A1 | 10/2002 | Bechtold-Peters et al. |
| 2005/0119486 A1 | 6/2005 | Ohta et al. |
| 2005/0245565 A1 | 11/2005 | Ohta et al. |
| 2006/0275357 A1 | 12/2006 | Oomura et al. |

FOREIGN PATENT DOCUMENTS

| | | |
|---|---|---|
| CN | 1118254 A | 3/1996 |
| EP | 1 103 253 | 5/2001 |
| EP | 1 103 253 A2 | 5/2001 |
| EP | 1 270 006 A2 | 1/2003 |
| EP | 1 270 006 A3 | 1/2003 |
| JP | 2-704 | 1/1990 |
| JP | 9-309829 | 12/1997 |
| JP | 2001-151672 | 6/2001 |
| JP | 2001151672 A | 6/2001 |
| JP | 2003-73274 | 3/2003 |
| JP | 2003073274 A | 3/2003 |

(Continued)

OTHER PUBLICATIONS

Chowdary et al, Effect of Selected Binders and Disintergrants on the Dissolution Rate Nimesulide From Tablets, 2000, vol. 62, Issue 3, p. 224-228.*
Extended Search Report issued Jun. 3, 2013 in European Patent Application No. 08720658.7.
Russian Office Action issued Nov. 22, 2011, in Russia Patent Application No. 2009139917/20(056637) (with English translation) (date of filing the application Mar. 28, 2008).
Takeuchi et al., "Tabletting of solid dispersion particles consisting of indomethacin and porous silica parties", Chem., Pharm., Bull., 53(5) 487-491 (2005).
Office Action mailed Jul. 30, 2012, in co-pending U.S. Appl. No. 13/328,847.

(Continued)

*Primary Examiner* — Wu-Cheng Winston Shen
*Assistant Examiner* — Jean Cornet
(74) *Attorney, Agent, or Firm* — Kenneth H. Sonnenfeld; Bryte V. Kelly; King & Spalding LLP (57) ABSTRACT

To provide pharmaceutical preparation exhibiting satisfactory dissolution property in a wide pH range.
The pharmaceutical composition is characterized by containing (A) $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide, represented by the following formula (1), a pharmacologically acceptable salt thereof, or a hydrate of any of these, and (B) one or more species selected from the group consisting of a sugar alcohol and a water-swelling additive.

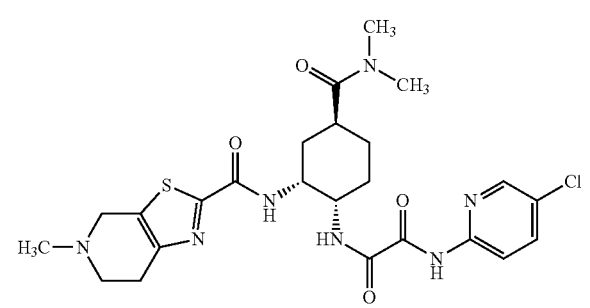

(1)

13 Claims, 8 Drawing Sheets

(56) References Cited

FOREIGN PATENT DOCUMENTS

| | | |
|---|---|---|
| JP | 2004518710 T | 6/2004 |
| JP | 2005-263816 | 9/2005 |
| JP | 2005263816 A | 9/2005 |
| RU | 2 271 805 C2 | 8/2004 |
| WO | WO 02/064124 A2 | 8/2002 |
| WO | WO 02/064124 A3 | 8/2002 |
| WO | WO 03/000680 A1 | 1/2003 |
| WO | WO 03000657 A1 | 1/2003 |
| WO | WO 03/016302 A1 | 2/2003 |
| WO | WO 03070279 A1 * | 8/2003 |
| WO | WO 03/097102 A1 | 11/2003 |
| WO | WO 2004/058715 A1 | 7/2004 |
| WO | WO 2004/110448 A1 | 12/2004 |

OTHER PUBLICATIONS

"Handbook for New Drug Approval Application 1993", Jiho, Inc., 1993, pp. 128-133 (with partial english translation).

Abu T.M. Serajuddin, "Salt formation to improve drug solubility", Advanced Drug Delivery Reviews, vol. 59, May 2007, pp. 603-616.

Alexander G.G. Turpie, "Oral, Direct Factor Xa Inhibitors in Development for the Prevention and Treatment of Thromboembolic Diseases", Arteriosclerosis, Thrombosis, and Vascular Biology, vol. 27, No. 6, XP002672841, Mar. 22, 2007, pp. 1238-1247.

Gombas et al., "Study of thermal behavior of sugar alcohols", Journal of Thermal Analysis and Calorimetry, vol. 73, 2003, pp. 615-621.

Jacob, et al., Indian Journal of Pharmaceutical Sciences, Sep. 1, 2007.

Nassab et al., "Physicochemical characterization of meloxicam-mannitol binary system", (Journal of Pharmaceutical and Biomedical Analysis 41 92006) 1191-1197.

Pharmacoat, Shin-Etsu Chemical Co., Ltd., Feb. 2005.

Vippagunta, et al. Advanced Drug Delivery Reviews, 48, 2001, p. 18.

Kubota et al., Response under 37 CFR 1.116, filed on Feb. 23, 2006 for U.S. Appl. No. 10/171,982, 11 pages.

Mathias et al., "Assessing the Risk of pH-Dependent Absorption for New Molecular Entities: A Novel in Vitro Dissolution Test, Physicochemical Analysis, and Risk Assessment Strategy," Mol. Pharmaceutics, 10, pp. 4062-4073, 2013.

Mitra et al., "Impaired Drug Absorption Due to High Stomach pH: A Review of Strategies for Mitigation of Such Effect to Enable Pharmaceutical Product Development," Mol. Pharmaceutics, 10, pp. 3970-3979, 2013.

Ware, "Physical Chemical Drug—Drug Interactions from Drug Discovery to Registration: New Opportunities for the Pharmaceutical Scientist to Impact Drug Development," Mol. Pharmaceutics, 10, pp. 3967-3969, 2013.

* cited by examiner

PHARMACEUTICAL COMPOSITION

CROSS-REFERENCE TO RELATED APPLICATIONS

This application is a continuation of U.S. Ser. No. 12/569,057, filed Sep. 29, 2009. U.S. Ser. No. 12/569,057 is continuation of International Application No. PCT/JP2008/000791, filed Mar. 28, 2008, which claims priority to Japanese Patent Application No. JP07-087327, filed Mar. 29, 2007, the entire contents of which are hereby incorporated by reference.

FIELD OF THE INVENTION

The present invention relates to a pharmaceutical composition useful as an anticoagulant, which comprises a component that is improved in dissolution property.

BACKGROUND OF THE INVENTION $N^1$-(5-chloropyridin-2-yl)-$N^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide, represented by formula (1), its pharmacologically acceptable salt, and their hydrates (hereinafter referred to as "compound (1)") are known to have a potent inhibitory action on activated blood coagulation factor X. Compound (1) also is known to be useful as a pharmaceutical, particularly such as an activated blood coagulation factor X inhibitor; a blood coagulation suppressor; an agent for preventing and/or treating thrombosis or embolism; an agent for preventing and/or treating thrombotic diseases; or an agent for preventing and/or treating cerebral infarction, cerebral embolism, heart infarction, angina pectoris, pulmonary embolism, Buerger's disease, deep vein thrombosis, universal intravascular coagulation syndrome, thrombus formation after artificial valve/joint replacement, thrombus formation and reocclusion after revascularization, multiple organ dysfunction syndrome (MODS), or thrombus formation during extracorporeal circulation or blood coagulation upon blood sample collection (Patent Documents 1 to 4).

(1)

Patent Document 1: WO 03/000657
Patent Document 2: WO 03/000680
Patent Document 3: WO 03/016302
Patent Document 4: WO 2004/058715

DISCLOSURE OF THE INVENTION

Problems to be Solved by the Invention

In a pharmaceutical composition for oral administration (e.g., tablet), the dissolution property of a pharmaceutically active ingredient thereof has an influential role in the efficacy and safety of the composition. Therefore, each country has established a standard rule pertaining to dissolution test method and its specification. Take Japan, the United States and Europe, for example. These countries are each publishing their Pharmacopoeias in which a method for carrying out a dissolution test is explained for guidance. Under such pharmacopeia, there are a variety of medium that are allowed to use for dissolution test (hereinafter referred to as "dissolution test medium"). These dissolution test medium have a pH that is adjusted to 1 to 8. Examples of the dissolution test medium described in the Pharmacopoeias of many countries include strongly acidic dissolution test medium (e.g., the first fluid for dissolution testing described in the Japanese Pharmacopoeia (hereinafter referred to as "JP 1st fluid") and 0.1N hydrochloric acid), dissolution test medium having a pH of 3 to 5 (e.g., acetic acid-sodium acetate buffer solution and McIlvaine buffer solution), dissolution test medium having a pH of 6.8 (e.g., the second fluid for dissolution testing described in the Japanese Pharmacopoeia (hereinafter referred to as "JP 2nd fluid") and phosphate buffer solution having a pH of 6.8), and water. A pharmaceutical drug product for oral administration is required to exhibit sufficient dissolution property when its dissolution test is carried out using such a medium.

Meanwhile, compound (1) is a basic compound and exhibits high solubility in a strong acidic aqueous solution, but its solubility decreases in a neutral pH aqueous solution (e.g., neutral buffer solution). Compound (1) itself exhibits excellent absorbability, if orally administered to a subject. On the other hand, an orally-administered pharmaceutical composition containing compound (1) that can be produced by use of a commonly used pharmaceutical excipient (e.g., lactose or cornstarch) turned out to have no good dissolution property.

Thus, an object of the present invention is to provide a pharmaceutical composition containing compound (1) as an active ingredient and exhibiting excellent dissolution property.

Means for Solving the Problems

In view of the foregoing, the present inventors have produced compositions containing compound (1) with a variety of pharmaceutical excipients, and have investigated the dissolution characteristics of the produced compositions. At last, surprisingly it has been found that the compound (1) dissolution property of such a composition can be enhanced by incorporating a sugar alcohol and/or a water-swelling additive into the composition, or by coating a composition containing compound (1) with one or more coating agents selected from among a cellulose derivative, a polyvinyl compound, an acrylate derivative, and a saccharide. The present invention has been accomplished on the basis of this finding.

The present invention is thus directed to (1) a pharmaceutical composition comprising (A) $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, represented by the following formula (1), a pharmacologically acceptable salt thereof, or a hydrate of any of these, and (B) one or more species selected from the group consisting of a sugar alcohol and a water-swelling additive.

[F2]

(1)

The present invention is also directed to pharmaceutical compositions as listed below:

(2) a pharmaceutical composition as described in (1) above, wherein the sugar alcohol is mannitol, xylitol, or erythritol;
(3) a pharmaceutical composition as described in (1) above, wherein the sugar alcohol is mannitol;
(4) a pharmaceutical composition as described in any of (1) to (3) above, wherein the water-swelling additive is pregelatinized starch or crystalline cellulose;
(5) a pharmaceutical composition as described in any of (1) to (3) above, wherein the water-swelling additive is pregelatinized starch;
(6) a pharmaceutical composition comprising, as an active ingredient, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, represented by the aforementioned formula (1), a pharmacologically acceptable salt thereof, or a hydrate of any of these, which composition is coated with at least one coating agent selected from among a cellulose derivative, a polyvinyl compound, an acrylate derivative, and a saccharide;
(7) a pharmaceutical composition as described in (6) above, wherein the coating agent is one or more species selected from among hypromellose, methyl cellulose, ethyl cellulose, hydroxypropyl cellulose, polyvinyl alcohol, povidone, Polyvinyl acetate, polyvinyl acetal diethylaminoacetate, aminoalkyl methacrylate copolymer RS, ethyl acrylate-methyl methacrylate copolymer dispersion, sucrose, and mannitol;
(8) a pharmaceutical composition as described in (6) above, wherein the coating agent is one or more species selected from among a cellulose derivative and a polyvinyl compound;
(9) a pharmaceutical composition as described in (6) above, wherein the coating agent is one or more species selected from among hypromellose, ethyl cellulose, and polyvinyl alcohol;
(10) a pharmaceutical composition as described in (6) above, wherein the coating agent is hypromellose;
(11) a pharmaceutical composition as described in any one of (1) to (5) above, which is coated with at least one coating agent selected from among a cellulose derivative, a polyvinyl compound, a acrylate derivative, and saccharide;
(12) a pharmaceutical composition as described in (11) above, wherein the coating agent is one or more species selected from among hypromellose, methyl cellulose, ethyl cellulose, hydroxypropyl cellulose, polyvinyl alcohol, povidone, Polyvinyl acetate, polyvinyl acetal diethylaminoacetate, aminoalkyl methacrylate copolymer RS, ethyl acrylate-methyl methacrylate copolymer dispersion, sucrose, and mannitol;
(13) a pharmaceutical composition as described in (11) above, wherein the coating agent is one or more species selected from among a cellulose derivative and a polyvinyl compound;
(14) a pharmaceutical composition as described in (11) above, wherein the coating agent is one or more species selected from among hypromellose, ethyl cellulose, and polyvinyl alcohol;
(15) a pharmaceutical composition as described in (11) above, wherein the coating agent is hypromellose;
(16) a pharmaceutical composition as described in any one of (6) to (15) above, wherein the coating agent is contained in an amount of 0.5 to 20 wt. % with respect to the total weight of the pharmaceutical composition;
(17) a pharmaceutical composition as described in any one of (1) to (16) above, wherein the compound represented by formula (1) is $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride;
(18) a pharmaceutical composition as described in any one of (1) to (15) above, wherein the compound represented by formula (1) is N-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate;
(19) a pharmaceutical composition as described in any one of (1) to (18) above, which has a dosage form of oral preparation;
(20) a pharmaceutical composition as described in any one of (1) to (19) above, which has a dosage form of solid preparation;
(21) a pharmaceutical composition as described in any one of (1) to (20) above, which has a dosage form of tablet, capsule, granule, or powder;
(22) a pharmaceutical composition as described in any one of (1) to (20) above, which has a dosage form of tablet;
(23) a pharmaceutical composition as described in any one of (1) to (22) above, wherein, when the composition is subjected to a dissolution test by the paddle method at a rotation rate of 50 rpm, the composition exhibits an average percent dissolution of the compound represented by formula (1), in a dissolution test medium having a pH of 6.8, of 60% or higher in 30 minutes after the start of the dissolution test and 70% or higher in 60 minutes after the start;
(24) a pharmaceutical composition as described in any one of (1) to (22) above, wherein, when the composition is subjected to a dissolution test by the paddle method at a rotation rate of 50 rpm, the composition exhibits an average percent dissolution of the compound represented by formula (1), in a dissolution test medium having a pH of 6.8, of 70% or higher in 30 minutes after the start of the dissolution test and 80% or higher in 60 minutes after the start;
(25) a pharmaceutical composition as described in any one of (1) to (24) above, wherein, when the composition is subjected to a dissolution test by the paddle method at a rotation rate of 50 rpm, the composition exhibits an average percent dissolution of the compound represented by formula (1), in a dissolution test medium having a pH of 4.5, of 85% or higher in 30 minutes after the start of the dissolution test;
(26) a method for enhancing dissolution rate of a compound represented by formula (1), the method employing a pharmaceutical composition as recited in (1) to (25); and
(27) a pharmaceutical composition as described in (1) to (25) above, wherein dissolution rate of the compound represented by formula (1) serving as an active ingredient is enhanced.

Advantageous Effect of the Invention

The present invention has made it possible to obtain a pharmaceutical composition for oral administration, which contains compound (1) and exhibits consistent dissolution characteristics while falling within the pH range of the aforementioned dissolution test medium. Thus the present invention provides an oral anticoagulant containing compound (1) as a pharmaceutically active ingredient and exhibiting favorable dissolution characteristics can be provided.

BEST MODES FOR CARRYING OUT THE INVENTION

The compound represented by formula (1) may be a hydrate of the compound, a pharmacologically acceptable salt of the compound, or a hydrate of the salt.

Examples of the salt of the compound represented by formula (1) include hydrochloride, sulfate, hydrobromide, hydroiodide, phosphate, nitrate, benzoate, methanesulfonate, 2-hydroxyethanesulfonate, p-toluenesulfonate, acetate, propanoate, oxalate, malonate, succinate, glutarate, adipate, tartrate, maleate, fumarate, malate, and mandelate.

Examples of preferred salts of the compound represented by formula (1) include hydrochloride, methanesulfonate, and p-toluenesulfonate. Of these, p-toluenesulfonate is particularly preferred.

Examples of the preferred compounds represented by formula (1) include the following ones:

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate; and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate (compound (1a), which is represented by the following formula (1a).

[F3]

(1a)

These compounds (I) may be produced by the methods disclosed in Patent Documents 1 to 4 or their analogic methods.

As one of the characteristics of the present invention, it can be said that when incorporated into a solid preparation, a coating agent serves to accelerate the dissolution of compound (1), which is a pharmaceutically active ingredient, from a solid preparation containing compound (1). In other words, the present invention provides a pharmaceutical composition for oral administration containing compound (1) and a coating agent, and exhibiting excellent dissolution property. No particular limitation is imposed on the form of the pharmaceutical composition for oral administration of the present invention containing compound (1) and a coating agent. The pharmaceutical composition of the invention encompasses not only coated solid preparations such as tablets but also various solid preparations containing a coating agent. As an example of such solid preparations containing compound (1), a coating agent forms a matrix in the solid preparation.

In the pharmaceutical composition for oral administration, examples of the coating agent employed for enhancing dissolution rate of compound (1) include coating agents generally employed in pharmaceutical manufacturing for coating tablets and granules therewith. Preferably, the coating agent has low solubility within a pH range in the intestine. Specifically, a coating agent which is difficult to dissolve within the pH range in the intestine is generally preferred, as compared with an enteric coating agent.

Specific examples of preferred coating agents include the following:

(1) cellulose derivatives such as hypromellose (hydroxypropyl methylcellulose), hydroxypropyl cellulose, ethyl cellulose, and methyl cellulose;

(2) polyvinyl compounds such as polyvinyl alcohol, povidone (polyvinylpyrrolidone), polyvinyl acetal diethylaminoacetate, and Polyvinyl acetate;

(3) acrylate derivatives such as aminoalkyl methacrylate copolymer RS and ethyl acrylate-methyl methacrylate copolymer dispersion; and (4) saccharides (including sugar alcohols) such as sucrose and mannitol, which are used as sugar-coating agents. These coating agents may be used singly or in combination or two or more species. Hypromellose or a hypromellose-based coating agent includes species such as hypromellose 2208, hypromellose 2906, and hypromellose 2910 having different viscosities (mPa·s). These species having different viscosities may be used singly or in combination of two or more species.

Among these, preferred are one or more species selected from the group consisting of cellulose derivatives (hypromellose, methyl cellulose, ethyl cellulose and hydroxypropyl cellulose); polyvinyl compounds (polyvinyl alcohol, povidone, Polyvinyl acetate and polyvinyl acetal diethylaminoacetate); acrylate derivatives (amino alkyl methacrylate copolymer RS and ethyl acrylate-methyl methacrylate copolymer dispersion); and saccharides (including sugar alcohols) (sucrose and mannitol).

Of these, one or more species selected from among cellulose derivatives and polyvinyl compounds are more preferred. Still more preferred are one or more species selected from among hypromellose, ethyl cellulose, and polyvinyl alcohol. Among them, hypromellose is particularly preferred.

In the present invention, the aforementioned coating agent and other additives required for preparing coating suspension (e.g., a plasticizer) may be incorporated in combination into the composition. Examples of the additives required for preparing coating suspension (e.g., a plasticizer) include Macrogols (polyethylene glycols having an av. weight molecular weight of 1,000 to 35,000) such as Macrogol 1000, Macrogol 1500, Macrogol 1540, Macrogol 4000, Macrogol 6000, Macrogol 8000, Macrogol 20000, and Macrogol 35000; glycerin fatty acid esters; sucrose fatty acid esters; castor oil; triethyl citrate; triacetin; and talc. The aforementioned coating agents may further contain the below-mentioned coloring agent, and the mixture may be incorporated into the pharmaceutical composition of the present invention.

From the viewpoint of enhancing dissolution rate of compound (1), the pharmaceutical composition of the present invention preferably contains a coating agent in an amount of 0.5 to 20 wt. %, more preferably 1 to 15 wt. %, particularly preferably 1.5 to 10 wt. %.

Next will be described coating of a solid preparation, which is a typical embodiment of the present invention.

In the present invention, a solid preparation containing compound (1) may be coated with the aforementioned coating agent through a widely known coating process for solid preparation coating. No particular limitation is imposed on the coating process, and for example, there may be employed a spray coating process in which a solution/dispersion of the coating agent is sprayed onto a solid preparation containing compound (1) by means of a fluidized bed coater or a pan coater; an dip coating process in which a solid preparation containing compound (I) is dipped in a coating suspension; and a dry coating process employing impact in a gas flow. The solid preparation containing compound (1) which has not been subjected to the coating process may be produced through a conventionally known process.

Thus, the pharmaceutical composition of the present invention may be produced by preparing a solid preparation containing compound (1) as a pharmaceutically active ingredient through a known method and then coating the thus-prepared solid preparation with a coating agent.

No particular limitation is imposed on the solid preparation containing compound (1) which has not been subjected to the coating process. However, preferred embodiments will next be described.

When a solid preparation containing compound (1) was produced by use of a combination of lactose and cornstarch, which is a combination of diluents generally employed in the production of solid preparations such as tablets, the produced solid preparation exhibited unsatisfactory dissolution characteristics in the dissolution tests using a strong acidic test medium, a test medium having a pH of 3 to 5, and water. In contrast, a solid preparation (1) containing compound (1) with sugar alcohol, and a solid preparation (2) containing compound (1) and a water-swelling additive have exhibited improved dissolution properties, as compared with those of a solid preparation containing compound (1) with lactose and cornstarch. Furthermore, a solid preparation (3) containing compound (I) and produced by use of sugar alcohol and a water-swelling additive in combination have exhibited satisfactory dissolution characteristics in the dissolution tests using a strong acidic test medium, a test mediumd having a pH of 3 to 5, and water.

Therefore, other preferred embodiments of the solid preparation containing compound (1) which has not been subjected to the coating process and which is employed in the present invention include the following: a solid preparation (1) containing compound (1) and sugar alcohol; a solid preparation (2) containing compound (1) and a water-swelling additive; and a solid preparation (3) containing compound (1) with sugar alcohol and a water-swelling additive. Of these, a solid preparation (3) containing compound (1) with sugar alcohol and a water-swelling additive is more preferred.

The water-swelling additive employed in the present invention refers to an additive for pharmaceuticals which swells with water added thereto. Examples of the water-swelling additive in the present invention include diluents and bases which are water-swellability. Specific examples of the water-swelling additive include pregelatinized starch, α-starch, crystalline cellulose, sodium starch glycolate, carmellose (carboxymethyl cellulose), carmellose calcium, croscarmellose sodium (croscarboxymethyl cellulose sodium), soybean lecithin, low-substituted hydroxypropyl cellulose, Powdered tragacanth, and bentonite. These additives may be used singly or in combination of two or more species.

Among these water-swelling additives, pregelatinized starch and crystalline cellulose are preferred, with pregelatinized starch being more preferred. As crystalline cellulose, Ceolus (product of Asahi Chemical Industry Co., Ltd.) is particularly preferred. As pregelatinized starch, PCS (product of Asahi Chemical Industry Co., Ltd.) and Starch 1500 (product of Colorcon Japan Limited) are particularly preferred.

Examples of preferred sugar alcohols which can improve dissolution of compound (1) include mannitol, erythritol, and xylitol. Of these, mannitol is particularly preferred.

To the composition of the present invention, a water-soluble diluent other than sugar alcohol may be added. Examples of the water-soluble diluent include fructose, purified sucrose, sucrose, purified sucrose spherical granules, lactose, anhydrous lactose, sucrose.starch spherical granules, semi-digested starch, glucose, glucose hydrate, powdered sugar, pullulan, and β-cyclodextrin. Other than saccharides, examples further include aminoethylsulfonic acid, maltose syrup powder, sodium chloride, citric acid, sodium citrate, glycine, calcium gluconate, L-glutamine, tartaric acid, potassium hydrogentartrate, ammonium carbonate, dextran 40, dextrin, calcium lactate, povidone, Macrogol (polyethylene glycol) 1500, Macrogol 1540, Macrogol 4000, Macrogol 6000, anhydrous citric, DL-malic acid, sodium hydrogenphosphate, potassium dihydrogenphosphate, and sodium dihydrogenphosphate.

The water-soluble diluent is preferably selected from saccharides. Specific examples include purified sucrose, sucrose, lactose, lactose granules, glucose, glucose hydrate, powdered sugar, and pullulan. Of these, lactose is more preferred.

From the viewpoint of improvement of dissolution of compound (1), the solid preparation containing compound (1) preferably contains a sugar alcohol in an amount of 0.01 to 99.0 wt. %, more preferably 20 to 80 wt. %, particularly preferably 40 to 60 wt. %. Also, the solid preparation containing compound (1) preferably contains a water-swelling additive in an amount of 0.01 to 90 wt. %, more preferably 0.1 to 80 wt. %, particularly preferably 5 to 50 wt. %.

In the case where the solid preparation contains the aforementioned water-swelling additive and sugar alcohol, the ratio of water-swelling additive to sugar alcohol in the preparation is preferably 0.05 to 50 parts by weight (sugar alcohol) to 1 part by weight (water-swelling additive), more preferably 1 to 10 parts by weight (sugar alcohol), particularly preferably 1.5 to 4 parts by weight (sugar alcohol).

In addition to the combination of the aforementioned sugar alcohol and water-swelling additive, the pharmaceutical composition containing compound (1) may further contain a water-insoluble diluent, a disintegrant, a binder, a fluidizing agent, a lubricant, a coloring agent, a polishing agent, etc., so long as the effect of the present invention is not impaired.

Examples of the water-insoluble diluent include L-aspartic acid, alginic acid, carmellose sodium, hydrous silicon dioxide, crospovidone, calcium glycerophosphate, magnesium silicate aluminate, calcium silicate, magnesium silicate, light anhydrous silicic acid, crystalline cellulose, cellulose powder, synthetic aluminum silicate, synthetic aluminum silicate-hydroxypropyl starch-crystalline cellulose, flour, wheat starch, wheat germ powder, wheat germ oil, rice powder, rice starch, cellulose acetate phthalate, titanium oxide, magnesium oxide, dihydroxyaluminum aminoacetate, calcium tertiary phosphate, talc, calcium carbonate, magnesium carbonate, precipitated calcium carbonate, natural aluminum silicate, cornstarch, granulated cornstarch, potato starch, hydroxypropyl cellulose, hydroxypropyl starch, calcium hydrogenphosphate anhydrous, granulated calcium hydrogenphosphate anhydrous, and calcium dihydrogenphosphate. Of these, crystalline cellulose and cellulose powder are preferred as a water-insoluble diluent.

Examples of the disintegrant include adipic acid, alginic acid, α-starch, sodium starch glycolate, carmellose carmellose calcium, carmellose sodium, hydrous silicon dioxide, calcium citrate, croscarmellose sodium, crospovidone, light anhydrous silicic acid, crystalline cellulose, synthetic aluminum silicate, wheat starch, rice starch, cellulose acetate phthalate, calcium stearate, low-substituted hydroxypropyl cellulose, cornstarch, powdered tragacanth, potato starch, hydroxyethylmethyl cellulose, hydroxypropyl starch, pregelatinized starch, monosodium fumarate, povidone, anhydrous citric, methyl cellulose, and calcium dihydrogenphosphate. Of these, crospovidone and sodium starch glycolate are preferred as a disintegrant.

Examples of the binder include maltose syrup powder, gum arabic, gum arabic powder, sodium alginate, propylene glycol alginate ester, hydrolyzed gelatin powder, hydrolyzed starch-light anhydrous silicic acid, fructose, carboxylvinyl polymer, carboxymethylethyl cellulose, hydrous silicon dioxide, agar powder, light anhydrous silicic acid, light anhydrous silicic acid-containing hydroxypropyl cellulose, crystalline cellulose, synthetic aluminum silicate, high-molecule polyvinylpyrrolidone, copolydone, flour, wheat starch, rice powder, rice starch, Polyvinyl acetate, cellulose acetate phthalate, dioctyl sodium sulfosuccinate, dihydroxyaluminum aminoacetate, sodium potassium tartrate, water, sucrose fatty acid ester, purified gelatin, purified sucrose, gelatin, D-sorbitol, dextrin, starch, cornstarch, tragacanth, powdered tragacanth, lactose, concentrate glycerin, sucrose, potato starch, hydroxyethyl cellulose, hydroxyethylmethyl cellulose, hydroxypropyl cellulose, hydroxypropyl starch, hydroxypropylmethyl cellulose 2208, hydroxypropylmethyl cellulose 2906, hydroxypropylmethyl cellulose 2910, hydroxypropylmethyl cellulose phthalate, vinylpyrrolidone-vinyl acetate copolymer, piperonyl butoxide, glucose, pregelatinized starch, fumaric acid, fumaric acid-stearic acid.polyvinyl acetal diethylaminoacetate.hydroxypropylmethyl cellulose 2910 mixture, pullulan, povidone, polyvinyl alcohol (completely saponified product), polyvinyl alcohol (partially saponified product), sodium polyphosphate, Macrogol 4000, Macrogol 6000, Macrogol 20000, D-mannitol, and methyl cellulose.

Examples of the fluidizing agent include hydrous silicon dioxide, light anhydrous silicic acid, crystalline cellulose, synthetic aluminum silicate, titanium oxide, stearic acid, calcium stearate, magnesium stearate, calcium tertiary phosphate, talc, cornstarch, and magnesium metasilicate aluminate.

Examples of the lubricant include cacao fat, carnauba wax, hydrous silicon dioxide, dry aluminum hydroxide gel, glycerin fatty acid ester, magnesium silicate, light anhydrous silicic acid, crystalline cellulose, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, cornstarch, potato starch, fumaric acid, stearyl sodium fumarate, Macrogol 600, Macrogol 4000, Macrogol 6000, beeswax, magnesium metasilicate aluminate, sodium laurate, and magnesium sulfate.

Examples of the coloring agent include yellow iron sesquioxide, iron sesquioxide, titanium oxide, orange essence, brown iron oxide, β-carotene, black iron oxide, Food Blue No. 1, Food Blue No. 2, Food Red No. 2, Food Red No. 3, Food Red No. 102, Food yellow No. 4, and Food yellow No. 5.

Examples of the polishing agent include carnauba wax, hardened oil, Polyvinyl acetate, white beeswax, titanium oxide, stearic acid, calcium stearate, polyoxyl 40 stearate, magnesium stearate, purified shellac, purified paraffin.carnauba wax mixture, cetanol, talc, colored silver foil, white shellac, paraffin, povidone, Macrogol 1500, Macrogol 4000, Macrogol 6000, beeswax, glycerin monostearate, and rosin. Of these, carnauba wax, titanium oxide, and talc are preferred as a polishing agent.

No particular limitation is imposed on the dosage form of the pharmaceutical composition of the present invention, so long as the drug preparation thereof can be orally administered to a subject. However, the dosage form is preferably a solid preparation, specifically in the form of tablet, granules, powder (including fine granules), or capsule. The solid preparation may be produced through a widely known production method therefor. In one exemplified procedure, the pharmaceutical composition of the present invention is prepared through mixing the aforementioned compound (1), a sugar alcohol and/or a water-swelling additive, and optional additives such as a disintegrant, a binder, a fluidizing agent, a lubricant, a coloring agent, and a polishing agent, and the mixture is processed through, for example, the method of producing solid preparations described in the general rules for preparations in the Japanese Pharmacopoeia.

When the pharmaceutical composition of the present invention is in the dosage form of granules, the granules may be produced through blending compound (1) with a sugar alcohol and/or a water-swelling additive and optional additives such as a diluent, a binder, a disintegrant, and other appropriate members, and granulating the thus-obtained uniform mixture through an appropriate technique. Additionally, the thus-produced granules may be coated with a coating agent by means of a fluidized bed coater through spraying a suspension/solution of the coating agent onto the granules.

When the pharmaceutical composition of the present invention is in the dosage form of powder, the powder (or microgranules) may be produced through blending compound (1) with a sugar alcohol and/or a water-swelling additive and optional additives such as a diluent, a binder, a disintegrant, and other appropriate members, to thereby form a uniform admixture, and pulverizing or micro-granulating the thus-obtained admixture through an appropriate technique. Additionally, the thus-produced powder (or microgranules) granules may be coated with a coating agent by means of a fluidized bed coater through spraying a suspension/solution of the coating agent onto the powder (or microgranules).

When the pharmaceutical composition of the present invention is in the dosage form of capsule, the aforementioned granules or powder may be encapsulated with coating capsules.

When the pharmaceutical composition of the present invention is in the dosage form of tablet, tablets may be produced directly through compression molding of a powder mixture containing the aforementioned compound (1) and acceptable additives for pharmaceuticals, preferably a powder mixture containing the aforementioned compound (1), a sugar alcohol and/or a water-swelling additive, and acceptable additives for pharmaceuticals. Alternatively, the tablets may be produced through granulating a powder mixture containing the aforementioned compound (1) and acceptable additives for pharmaceuticals, preferably a powder mixture containing the aforementioned compound (1), a sugar alcohol and/or a water-swelling additive, and acceptable additives for pharmaceuticals, through a technique such as fluidized bed granulation or agitation granulation, followed by compression molding of the formed granules. The pressure of compression molding may be determined within an appropriate range, so long as the effect of the present invention is not impaired. The compression molding is preferably performed at 6 to 15 kN. No particular limitation is imposed on the shape of the tablets, and lens-shape, disk-shape, round, oval, triangle, and polygon shapes such as lozenges are preferred. Additionally, the thus-produced tablets may be further coated with a coating agent by means of a pan coater through spraying a suspension/solution of the coating agent onto the tablets.

The pharmaceutical composition of the present invention generally has a compound (1) content of 10 to 30 wt. % (as free form), preferably 12 to 25 wt. %. Particularly when the pharmaceutical composition of the present invention is in the table form, the compound (1) content (as free form) is generally 1 to 100 mg/tablet, preferably 5 to 75 mg/tablet, more preferably 15 to 60 mg/tablet.

The compound (1) dissolution property of the pharmaceutical composition of the present invention can be evaluated by, for example, dissolution tests disclosed in the Japanese Pharmacopoeia, the United States Pharmacopoeia (USP), and the European Pharmacopoeia. Examples of the test medium employed in the dissolution tests will next be described.

Non-limiting examples of the aforementioned strongly acidic dissolution test medium include the JP 1st fluid described in the Japanese Pharmacopoeia, and "USP 0.1N HCl, Simulated Gastric Fluid without Enzyme" described in the United States Pharmacopoeia.

Non-limiting examples of the dissolution test medium (pH: 6.8) include the JP 2nd fluid and phosphate buffer (pH: 6.8) described in the Japanese Pharmacopoeia; "USP Phosphate Buffer (pH: 6.8), Simulated Intestinal Fluid without Enzyme" described in the United States Pharmacopoeia; and Phosphate Buffer Solution (pH: 6.8) described in the European Pharmacopoeia.

The dissolution test medium (pH: 3 to 5) may be a test medium having a pH of 4.0 or 4.5. Specific examples include acetic acid-sodium acetate buffer described in the Japanese Pharmacopoeia; "USP Acetate Buffer" described in the United States Pharmacopoeia; and Acetate Buffer Solution (pH: 4.5) described in the European Pharmacopoeia. Alternatively, a diluted McIlvaine buffer (pH: 4.0) may also be employed.

However, the dissolution test medium (pH: 3 to 5) is not limited to the above examples.

These dissolution test medium are prepared through methods described in the corresponding Pharmacopoeia. When the employed dissolution test medium is a buffer solution, variation of the pH of the test medium specified in the corresponding Pharmacopoeia is preferably controlled to fall within a range of ±0.05.

When the composition is subjected to the dissolution test disclosed in the Japanese Pharmacopoeia (paddle method; at a rotation rate of 50 rpm), the composition preferably exhibit an average percent dissolution of compound (1), in a dissolution test medium having a pH of 6.8, of 60% or higher in 30 minutes after the start of the dissolution test and 70% or higher in 60 minutes after the start, more preferably 70% or higher in 30 minutes after the start and 80% or higher in 60 minutes after the start.

When the composition is subjected to the dissolution test disclosed in the Japanese Pharmacopoeia (paddle method; at a rotation rate of 50 rpm), the composition preferably exhibit an average percent dissolution of compound (1), in a dissolution test medium having a pH of 4.5, of 85% or higher in 30 minutes after the start of the dissolution test.

As used herein, the "average percent dissolution" refers to an average of percent dissolution values obtained from at least 3, preferably 6, more preferably 12 solid preparation samples of a single type.

EXAMPLES

The present invention will next be described in detail by way of examples, which should not be construed as limiting the invention thereto.

Example 1

Effect of Diluent

Tablets containing compound 1a were produced according to the formulations shown in Table 1 (all values in the table are on "mg" basis). The tablets were analyzed in terms of dissolution of compound 1a in accordance with the method 2 (paddle method) at a rotation rate of 50 rpm described in the Japanese Pharmacopoeia. Percent dissolution was calculated by averaging percent dissolution values of three tablets of the same formulation. An acetate buffer (pH: 4.0) was employed as a dissolution test medium. The acetate buffer (pH: 4.0) was prepared through the following procedure.

Method for preparing the acetate buffer (pH: 4.0): Sodium acetate trihydrate (2.45 g) and glacial acetic acid (4.9 g) were weighed, and purified water was added thereto, so that the total volume of the buffer came to 1,000 mL.

(Preparation of Tablets)

In each case, ingredients shown in Table 1 excepting hydroxypropyl cellulose and magnesium stearate were mixed by means of a mortar, and the mixture was granulated by use of aqueous hydroxypropyl cellulose solution. The thus-produced granules were mixed with magnesium stearate, to thereby yield granules were compressed into tablets using 8.0 mmϕ round shaped dies and punches at 7.8 kN of compression force, to thereby yield tablets of interest. In Example 1, the following materials were employed as the ingredients listed in Table 1.

Lactose [Pharmatose 200M (trade name)], mannitol [Mannit (trade name)], cornstarch [Cornstarch (trade name)], crystalline cellulose [Ceolus (trade name)], pregelatinized starch [PCS (trade name)], sodium starch glycolate [Primojel (trade name)], hydroxypropyl cellulose [HPC-L (trade name)], and magnesium stearate [HyQual (trade name)].

TABLE 1

| | Formulation (mg) | | | | |
|---|---|---|---|---|---|
| | A | B | C | D | E |
| Compound 1a | 40.41 | 40.41 | 40.41 | 40.41 | 40.41 |
| Lactose | 99.79 | | 99.79 | | |
| Mannitol | | 99.79 | | 99.79 | 99.79 |
| Cornstarch | 42.8 | 42.8 | | | |
| Crystalline cellulose | | | | | 42.8 |
| Pregelatinized starch | | | 42.8 | 42.8 | |
| Sodium starch glycolate | 10.0 | 10.0 | 10.0 | 10.0 | 10.0 |
| Hydroxypropyl cellulose | 6.0 | 6.0 | 6.0 | 6.0 | 6.0 |
| Mg stearate | 1.0 | 1.0 | 1.0 | 1.0 | 1.0 |
| Weight/tablet | 200.0 mg | 200.0 mg | 200.0 mg | 200.0 mg | 200.0 mg |

Figure 1:
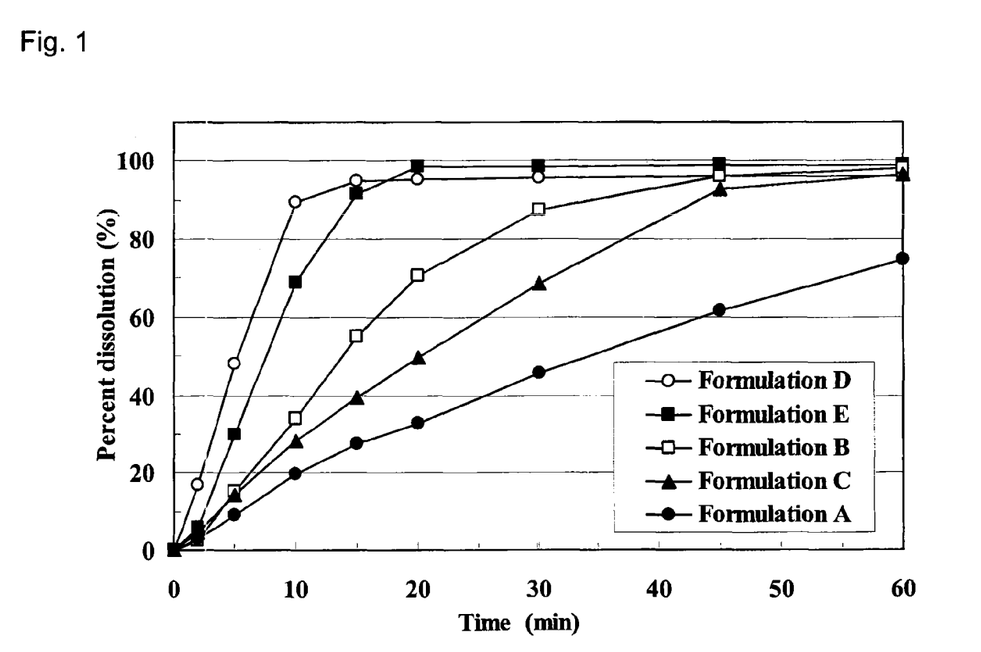
FIG. 1 A graph showing dissolution properties of tablets having formulations A to E (dissolution test medium: acetate buffer solution (pH 4.0)).

FIG. 1 shows the results of the dissolution test (in acetate buffer solution (pH: 4.0)) of the tablets of formulations A to E in Table 1. As is clear from FIG. 1, tablets containing mannitol as a diluent (formulation B), those containing pregelatinized starch as a diluent (formulations C and D), and those containing crystalline cellulose as a diluent (formulation E) exhibited excellent compound 1a dissolution characteristics. Tablets containing mannitol and pregelatinized starch as a diluent (formulation D) and those containing mannitol and crystalline cellulose as a diluent (formulation E) exhibited more excellent compound 1a dissolution characteristics. In contrast, when lactose and cornstarch, which are generally employed as diluent, were employed (formulation A), the compound 1a dissolution property was unsatisfactory.

Example 2

Studies on Disintegrant

Ingredients shown in Table 2 (all values in the table are on "mg" basis) excepting hydroxypropyl cellulose and magnesium stearate were mixed by means of a mortar, and the mixture was granulated by use of aqueous hydroxypropyl cellulose solution. The thus-produced granules were mixed with magnesium stearate, to thereby yield granules were compressed into tablets using 8.0 mm# round shaped dies and punches at 7.8 kN of compression force, to thereby yield tablets of interest.

In a manner similar to that of Example 1, the produced tables were analyzed in terms of dissolution property. The percent dissolution was calculated by averaging percent dissolution values of three tablet samples.

In Example 2, the following disintegrants were employed and compared with one another.

Sodium starch glycolate [Primojel (trade name)], crospovidone [Polyplasdone (trade name)], carmellose calcium [ECG-505 (trade name)], and low-substituted hydroxypropyl cellulose [L-HPC (trade name)].

TABLE 2

| | Formulation (mg) | | | |
|---|---|---|---|---|
| | F | G | H | I |
| Compound 1a | 40.41 | 40.41 | 40.41 | 40.41 |
| Mannitol | 102.59 | 102.59 | 102.59 | 102.59 |
| Pregelatinized starch | 40.0 | 40.0 | 40.0 | 40.0 |
| Sodiuml starch glycolate | 10.0 | | | |
| Crospovidone | | 10.0 | | |
| Carmellose Ca | | | 10.0 | |
| Low-substituted hydroxypropyl cellulose | | | | 10.0 |
| Hydroxypropyl cellulose | 6.0 | 6.0 | 6.0 | 6.0 |
| Mg stearate | 1.0 | 1.0 | 1.0 | 1.0 |
| Weight/tablet | 200.0 mg | 200.0 mg | 200.0 mg | 200.0 mg |

Figure 2:
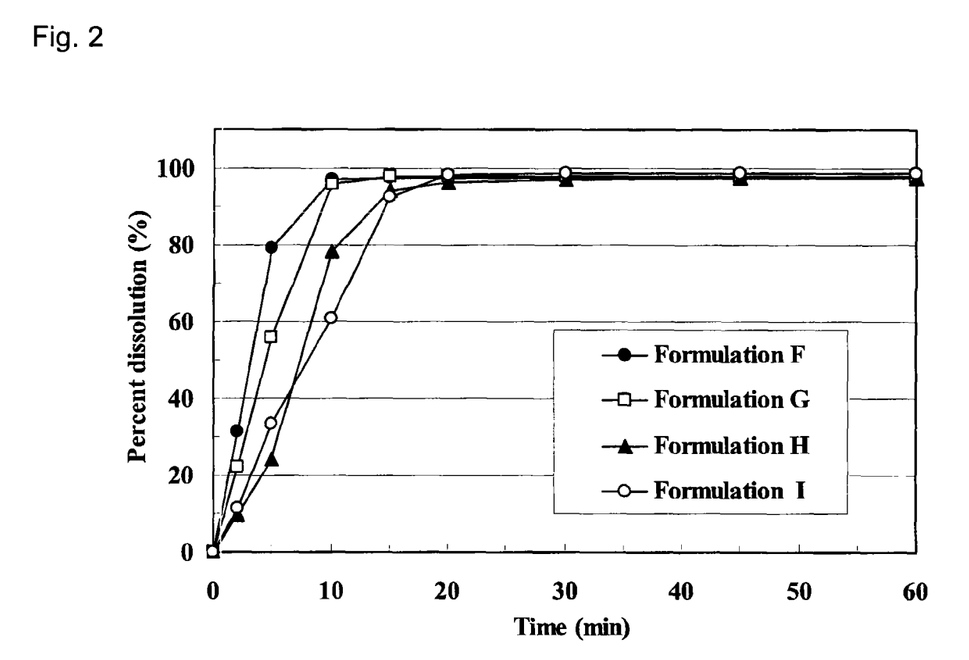
FIG. 2 A graph showing dissolution properties of tablets having formulations F to I (dissolution test medium: acetate buffer solution (pH 4.0)).

FIG. 2 shows the results of the dissolution test (in acetate buffer solution (pH: 4.0)) of the tablets of formulations F to I in Table 2. As is clear from FIG. 2, tablets containing sodium starch glycolate or crospovidone as a disintegrant exhibited an excellent compound 1a dissolution property.

Example 3

Tablets containing compound 1a were produced according to the formulations shown in Table 3 (all values in the table are on "mg" basis), and were analyzed in terms of dissolution of compound 1a in a manner similar to that of Example 1, except that 0.1N hydrochloric acid (USP 0.1N HCl), water, and phosphate buffer solution (pH: 6.8) [USP Phosphate buffer solution (pH: 6.8)] were employed as dissolution test medium. In each tablet production, ingredients shown in Table 3 excepting hydroxypropyl cellulose and magnesium stearate were mixed together, and the mixture was granulated by means of a fluidized bed granulator through spraying aqueous hydroxypropyl cellulose solution onto the mixture. The thus-produced granules were mixed with magnesium stearate, to thereby yield granules were compressed into tablets using 8.5 mmϕ round shaped dies and punches at 7.5 kN of compression force, to thereby yield tablets of interest. The percent dissolution was calculated by averaging percent dissolution values of six tablet samples.

TABLE 3

| | Formulation | | | | |
|---|---|---|---|---|---|
| | J | K | L | M | N |
| Compound 1a | 40.4 | 40.4 | 40.4 | 40.4 | 40.4 |
| Lactose | 99.2 | | 99.2 | | |
| Mannitol | | 99.2 | | 99.2 | 99.2 |
| Cornstarch | 42.0 | 42.0 | | | |
| Crystalline cellulose | | | | | 42.0 |
| Pregelatinized starch | | | 42.0 | 42.0 | |
| Crospovidone | 10.7 | 10.7 | 10.7 | 10.7 | 10.7 |
| Hydroxypropyl cellulose | 6.1 | 6.1 | 6.1 | 6.1 | 6.1 |
| Mg stearate | 1.6 | 1.6 | 1.6 | 1.6 | 1.6 |
| Weight/tablet | 200.0 mg | 200.0 mg | 200.0 mg | 200.0 mg | 200.0 mg |

Figure 3:
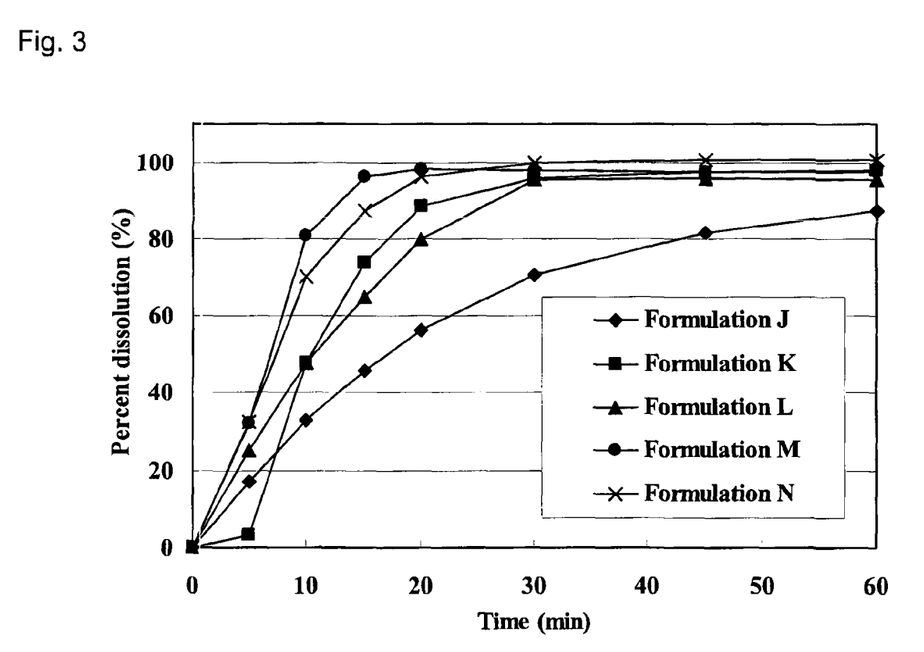
FIG. 3 A graph showing dissolution properties of tablets having formulations J to N (dissolution test medium: 0.1N hydrochloric acid).
Figure 4:
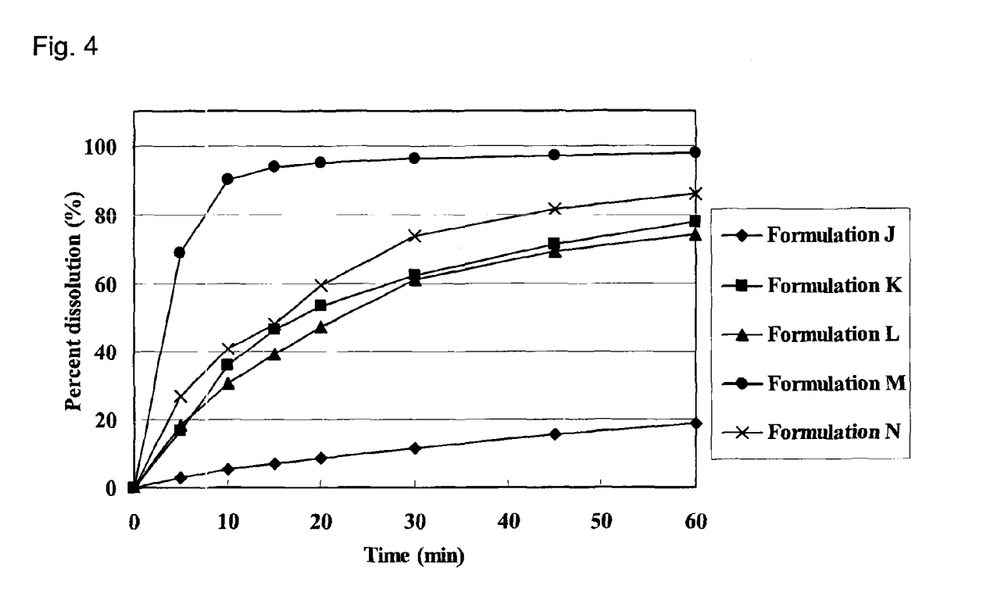
FIG. 4 A graph showing dissolution properties of tablets having formulations J to N (dissolution test medium: water).
Figure 5:
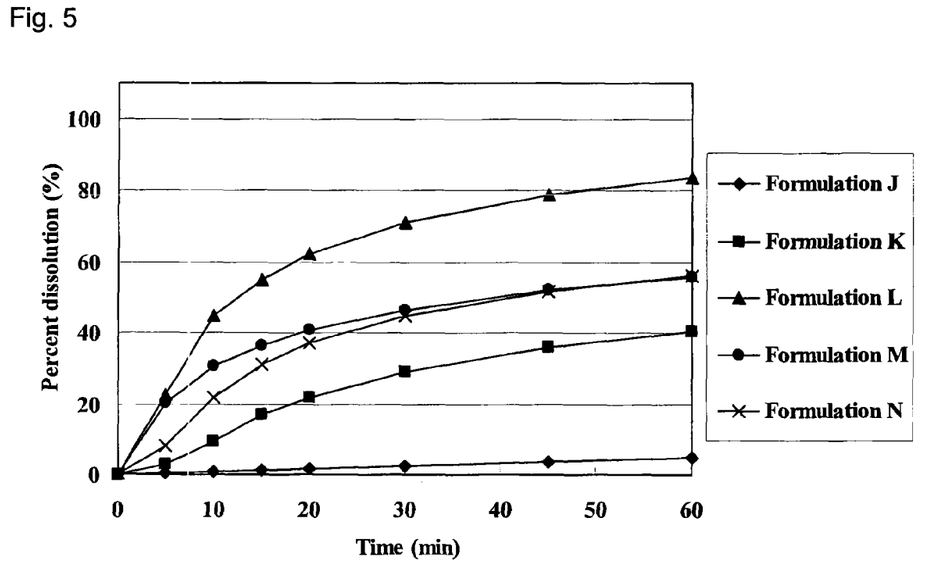
FIG. 5 A graph showing dissolution properties of tablets having formulations J to N (dissolution test medium: phosphate buffer solution (pH 6.8)).

FIGS. 3 to 5 show the results of the dissolution test (in 0.1N hydrochloric acid, in water, and in phosphate buffer solution (pH: 6.8)) of the tablets of formulations J to N in Table 3. As is clear from FIGS. 3 to 5, tablets containing mannitol and pregelatinized starch exhibited an excellent compound 1a dissolution property in 0.1N hydrochloric acid and in water.

Example 4

Studies on Coating Agent

Figure 6:
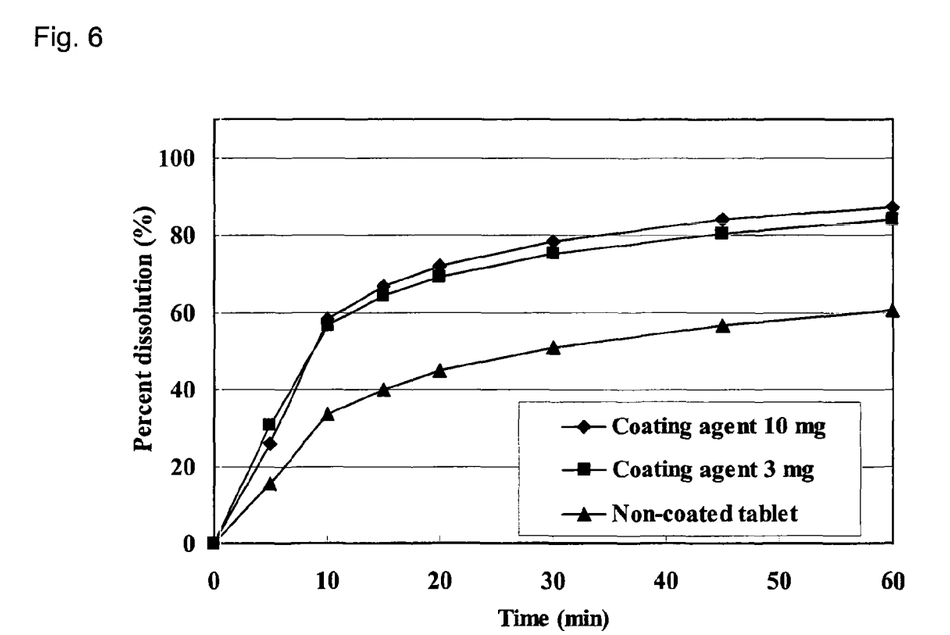
FIG. 6 A graph showing dissolution properties of tablets coated with hypromellose (dissolution test medium: phosphate buffer solution (pH 6.8)).

Ingredients shown in Table 4 (all values in the table are on "mg" basis) excepting hydroxypropyl cellulose and magnesium stearate were mixed together, and the mixture was granulated by means of a fluidized bed granulator through spraying aqueous hydroxypropyl cellulose solution onto the mixture. The thus-produced granules were mixed with magnesium stearate, to thereby yield granules were compressed into tablets using 8.5 mmϕ round shaped dies and punches at about 10 kN of compression force, to thereby yield tablets of interest. The tables were coated with a commercial coating agent by means of a pan coater (Hicoater Multi, product of Freund Corporation), to thereby prepare film-coated tablets. As the coating agent, a pre-mixed product [OPADRY 03F42132 (trade name)], predominantly containing hypromellose, was used. In a manner similar to that of Example 1, tablets coated with OPADRY 03F42132 (3 mg), those coated with OPADRY 03F42132 (10 mg), and those not coated (non-coated tablets) were subjected to dissolution tests in phosphate buffer solution (pH: 6.8) [USP Phosphate buffer solution (pH: 6.8)]. The results are shown in FIG. 6. The percent dissolution was calculated by averaging percent dissolution values of six tablet samples.

Figure 7:
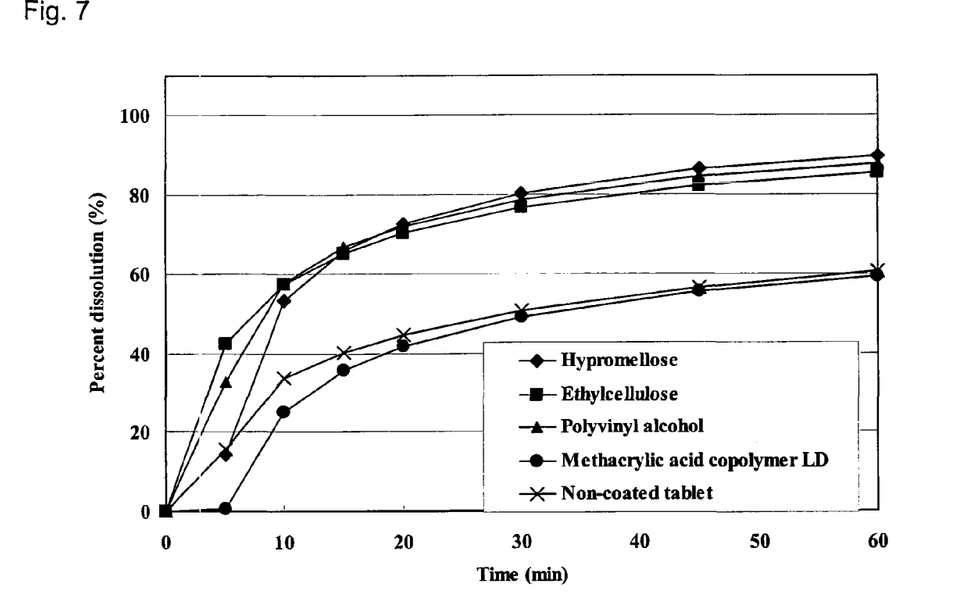
FIG. 7 A graph showing dissolution properties of tablets coated with various coating agents (dissolution test medium: phosphate buffer solution (pH 6.8)).

Separately, by means of a pan coater (Hicoater Mini, product of Freund Corporation), film-coated tablets were produced through coating non-coated tablets with a coating agent [OPADRY 03F42132 (trade name)] predominantly containing hypromellose, generally employed as a rapidly soluble coating agent; a coating agent [OPADRY AMB (trade name)], predominantly containing polyvinyl alcohol, generally employed as a rapidly soluble coating agent; a coating agent [Aquacoat-ECD (trade name)], predominantly containing ethyl cellulose, serving as a pH-independent sustained-release-type coating agent; or a coating agent [Eudragit L30-D55 (trade name)], predominantly containing methacrylate copolymer LD, serving as a pH-dependent enteric coating agent, the amount coating agent in each case being 10 mg. In a manner similar to that of Example 1, these film-coated tablets were subjected to dissolution tests in phosphate buffer solution (pH: 6.8) [USP Phosphate buffer solution (pH: 6.8)].

The results are shown in FIG. 7. The percent dissolution was calculated by averaging percent dissolution values of six tablet samples.

Figure 8:
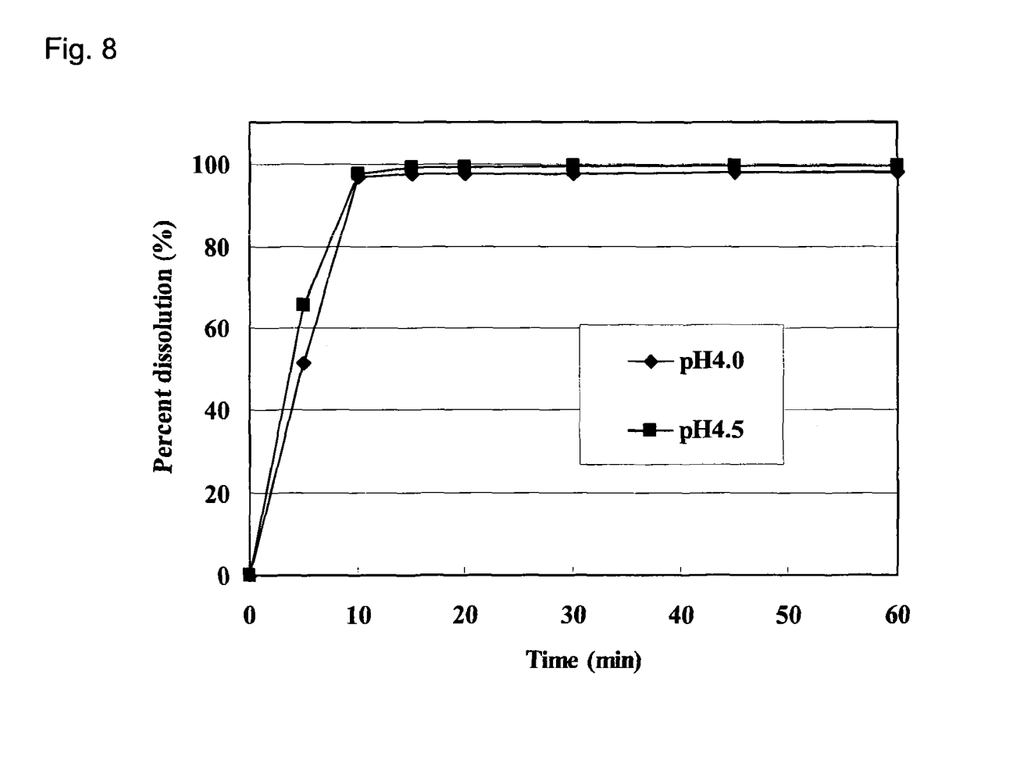
FIG. 8 A graph showing dissolution properties of tablets coated with hypromellose (dissolution test medium: acetate buffer solutions (pH 4.0) and (pH 4.5)).

Further, by means of a pan coater (Hicoater Multi, product of Freund Corporation), film-coated tablets were produced through coating non-coated tablets with a coating suspension (10 mg) containing about 60% of hypromellose [TC-5 (trade name)]. In a manner similar to that of Example 1, these film-coated tablets were subjected to dissolution tests in acetate buffer solutions (pH: 4.0) and (pH: 4.5). The results are shown in FIG. 8. The percent dissolution was calculated by averaging percent dissolution values of six tablet samples.

TABLE 4

| Ingredients (mg) | Formulation |
|---|---|
| Compound 1a | 40.4 |
| Mannitol | 99.2 |
| Pregelatinized starch | 42.0 |
| Crospovidone | 10.7 |
| Hydroxypropyl cellulose | 6.1 |
| Mg stearate | 1.6 |
| Weight/tablet | 200.0 mg |

As is clear from FIG. 6, quite surprisingly, tablets coated with a hypromellose-based agent exhibited an improved compound 1a dissolution property at a pH of 6.8, as compared with non-coated tablets. Furthermore, the amount of coating agent did not affect the dissolution behavior.

As is clear from FIG. 7, tablets coated with a coating agent other than an enteric coating agent exhibited a considerably excellent dissolution property.

As is clear from FIG. 8, tablets coated with a hypromellose-based agent exhibited an equivalently excellent dissolution property in acetate buffer solution (pH: 4.0) and in acetate buffer solution (pH: 4.5).

The invention claimed is:

1. A pharmaceutical composition in the form of a tablet wherein the tablet comprises:
    (A) N'-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, represented by formula (1):

(1)

pharmacologically acceptable salt thereof, or a hydrate thereof;

(B) a sugar alcohol that is one or more species selected from the group consisting of mannitol, xylitol, and erythritol, wherein the sugar alcohol is present in an amount from 40 to 60 wt. % with respect to the total weight of the pharmaceutical composition; and (C) a water-swelling additive selected from pregelatinized starch, crystalline cellulose or a combination thereof; wherein the ratio of sugar alcohol to water-swelling additive is 1.5 to 4 parts by weight sugar alcohol to 1 part by weight water-swelling additive;

and wherein the tablet is coated with at least one coating agent selected from the group consisting of hypomellose, methyl cellulose, ethyl cellulose, hydroxypropyl cellulose, and polyvinyl alcohol, and wherein the coating agent is present in the amount of 1.5 to 5 wt. % with respect to the total weight of the pharmaceutical composition.

2. The pharmaceutical composition according to claim 1, wherein the sugar alcohol is mannitol.

3. The pharmaceutical composition according to claim 1, wherein the water-swelling additive is pregelatinized starch.

4. The pharmaceutical composition according to claim 1, wherein the coating agent is one or more species selected from the group consisting of hypromellose, ethyl cellulose, and polyvinyl alcohol.

5. The pharmaceutical composition according to claim 1, wherein the coating agent is hypromellose.

6. The pharmaceutical composition according to claim 1, wherein the compound represented by formula (1), a pharmacologically acceptable salt thereof, or a hydrate of any of these is $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide hydrochloride.

7. The pharmaceutical composition according to claim 1, wherein the compound represented by formula (1), a pharmacologically acceptable salt thereof, or a hydrate thereof is $N^1$-(5-chloropyridin-2-yl)-$N^2$-((1 S,2R,4S)-4-[(dimethylamino)carbonyl]-2-{[(5-methyl-4,5,6,7-tetrahydrothiazolo [5,4-c]pyridin-2-yl)carbonyl]amino}cyclohexyl)ethanediamide p-toluenesulfonate monohydrate.

8. The pharmaceutical composition according to claim 1, wherein the compound represented by the formula (I) is present in an amount of 12 to 25 wt. % with respect to the total weight of the pharmaceutical composition.

9. The pharmaceutical composition according to claim 1, wherein the water-swelling additive is present in an amount of 10 to 30 wt. % with respect to the total weight of the pharmaceutical composition.

10. The pharmaceutical composition according to claim 1, wherein the coating agent is present in an amount of 2-5 wt. % with respect to the total weight of the pharmaceutical composition.

11. The pharmaceutical composition according to claim 1, wherein the compound represented by the formula (I) is present in an amount of 15 to 60 wt. % with respect to the total weight of the pharmaceutical composition.

12. The pharmaceutical composition according to claim 1, wherein the pharmaceutical composition exhibits an average percent dissolution of the compound represented by the formula (I) in a dissolution test medium having a pH of 6.8 of 60% or higher in 30 minutes after the start of the dissolution test and 70% or higher in 60 minutes after the start of the dissolution test when the pharmaceutical composition is subjected to a dissolution test by a paddle method at a rotation of 50 rpm.

13. The pharmaceutical composition according to claim 1, wherein the pharmaceutical composition exhibits an average percent dissolution of the compound represented by the formula (I) in a dissolution test medium having a pH of 6.8 of 70% or higher in 30 minutes after the start of the dissolution test and 80% or higher in 60 minutes after the start of the dissolution test when the pharmaceutical composition is subjected to a dissolution test by a paddle method at a rotation of 50 rpm.

* * * * *